(12) United States Patent
Natarajan et al.

(10) Patent No.: US 7,645,423 B2
(45) Date of Patent: Jan. 12, 2010

(54) OPTICAL MICRO PLUGS FOR MULTICHANNEL AND MULTILAYER PHARMACEUTICAL DEVICE

(75) Inventors: Govindarajan Natarajan, Poughkeepsie, NY (US); David H. Gabriels, Cold Spring, NY (US); Mark W. Kapfhammer, Poughkeepsie, NY (US); Richard A. Shelleman, Poughkeepsie, NY (US); Kurt A. Smith, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 683 days.

(21) Appl. No.: 10/711,071

(22) Filed: Aug. 20, 2004

(65) Prior Publication Data
US 2006/0039831 A1 Feb. 23, 2006

(51) Int. Cl.
*B01L 3/00* (2006.01)
(52) U.S. Cl. .................................... 422/102
(58) Field of Classification Search .................. 422/102
See application file for complete search history.

(56) References Cited

U.S. PATENT DOCUMENTS

| | | | |
|---|---|---|---|
| 5,534,328 A | 7/1996 | Ashmead et al. | |
| 5,575,872 A | 11/1996 | Tsukada et al. | |
| 5,843,385 A | 12/1998 | Dugan | |
| 5,961,930 A | 10/1999 | Chatterjee et al. | |
| 5,961,932 A | 10/1999 | Ghosh et al. | |
| 5,965,092 A | 10/1999 | Chatterjee et al. | |
| 5,976,472 A | 11/1999 | Chatterjee et al. | |
| 5,993,750 A | 11/1999 | Ghosh et al. | |
| 6,033,544 A | 3/2000 | Demers et al. | |
| 6,036,927 A | 3/2000 | Chatterjee et al. | |
| 6,463,647 B1 | 10/2002 | Dannoux | |
| 2004/0043479 A1* | 3/2004 | Briscoe et al. ........... 435/288.5 |
| 2004/0129371 A1 | 7/2004 | Natarajan et al. | |

FOREIGN PATENT DOCUMENTS

CN 2390207 Y 8/2000

(Continued)

OTHER PUBLICATIONS

IBM Technical Disclosure Bulletin "Fluidic Logic Block", F. J. Campagna and L. J. Reed, vol. 14, No. 10, Mar. 1972.

(Continued)

*Primary Examiner*—Walter D Griffin
*Assistant Examiner*—Bobby Ramdhanie
(74) *Attorney, Agent, or Firm*—DeLio & Peterson, LLC; Kelly M. Nowak; Wenjie Li (57) ABSTRACT

A method of making and the resultant micro well plate that includes a plurality of greensheets, either laminated or sintered together, whereby these greensheets have a plurality of vertical micro well reaction chamber openings therein, and optionally a plurality horizontal channels connecting selected well reaction chamber openings. The vertical micro well reaction chambers have at, at least one end thereof a plurality of optical micro plugs which are aligned to the vertical micro well reaction chamber openings. The plurality of optical micro plugs allow for the micro well plate to be integrated with macro analytical instrumentation for the analysis, examination, and/or testing of chemicals, reagents or samples provided within the vertical micro well reaction chamber openings.

20 Claims, 3 Drawing Sheets

FOREIGN PATENT DOCUMENTS

| | | |
|---|---|---|
| EP | 0 021 659 A1 | 5/1980 |
| EP | 1314472 A1 | 5/2003 |
| WO | WO 00/21659 | 4/2000 |
| WO | WO 01/41931 A2 | 6/2001 |
| WO | WO2004/063103 | 7/2004 |

OTHER PUBLICATIONS

European Search Report Dated December 23, 2005 From Counterpart Application EP 05 10 7349.

\* cited by examiner

OPTICAL MICRO PLUGS FOR MULTICHANNEL AND MULTILAYER PHARMACEUTICAL DEVICE

BACKGROUND OF INVENTION

CROSS-REFERENCE TO RELATED APPLICATIONS

Aspects of the present invention are related to subject matter disclosed in co-pending application entitled "Multichannel and Multilayer Pharmaceutical Device," U.S. Publication No. 2004 0129371, filed on Jan. 7, 2003, and assigned to the assignee of the present invention, the subject matter of which is hereby incorporated by reference.

BACKGROUND OF THE INVENTION

1. Field of the Invention

The present invention relates generally to a device that can be used in the medical and pharmaceutical industries for testing numerous combinations of drug interactions, and in particular, to a structure and method of forming a micro plug in a multilayer ceramic (MLC) biochip for use in high-speed sample testing and analysis.

2. Description of Related Art

A critical aspect of the medical and pharmaceutical industries is the research, testing and analysis of chemical samples, biological samples, drug interactions, drug activity, and the like, such as, for example, by immunoassays. These types of research, testing and analysis often require the reaction (including biological activity) of chemical A to chemicals $B_1$-$B_n$, where n can be a large number, on the order of millions.

The use of plastic well plates is well known in the medical and pharmaceutical industry for supplying the various chemicals and biological samples therein. In so doing, an array of substances A and $B_1$-$B_n$ are provided within the well openings of the plastic plate, usually via pipettes, for the contact and interaction of these substances within the wells. Commercially available plastic plates include arrays of 96 and 384 well openings, having diameters typically of about 3 mm to about 4 mm, and depths of about ½ inch.

In the medical and pharmaceutical industries, there are currently numerous medical tests along with the continued research and development of both new medical tests and drug discoveries. As the demand increases for such medical tests, both new and existing, as well as increases in the need for new drugs or therapies, the requirement of multiple sampling throughput remains high. Also, in the research and development of new drugs, therapies and medical tests, since there are millions of chemicals and reactants to test for exhausting the endless possibilities of combinations, it often takes those companies involved in research and development years to bring a successful drug, therapy or either clinical tests or point of care tests to market.

With the current speed of computer assisted microfluidic scanning devices, it is possible to increase the rate at which bulk samples are analyzed or tested, such as by increasing the number of samples scanned and processed simultaneously, i.e., within a single run. Microfluidic scanning devices allow the integration and miniaturize of multiple laboratory processes into a single conventional chip size device by increasing the number of well openings in a given volume within the well plate. That is, an increased number of smaller micro holes and channels speeds up the process of researching, analyzing and testing the endless possibilities of combinations of chemicals and reactants. This use of a large number of well openings in a given volume within the well plate advantageously reduces the consumption of expensive chemicals/reagents used during analysis or testing (due to the smaller sizes of the wells), which in turn, lowers the manufacturing costs, increases sample throughput, provides faster end results due to faster analysis, provides high performance and success, and allows for an enormous scope of integration and ease of automation.

However, conventional plastic well plates are usually formed by extrusion, which is very limiting in that it does not provide exact precision of well opening diameters, nor does it provide desired locations of well openings within the array of wells formed in the plastic well plates. If well opening diameters and locations are not to exact specifications, such as is the case when forming an increased number of smaller well openings (well holes and channels) within plastic well plates, the precision of both analytical instrumentation used in introducing chemicals and reagents into the well openings as well as instrumentation for scanning the well openings will be imprecise. As such, the use of plastic well plates are not adequate for fabricating an increased number of well openings composed of smaller micro holes and channels, thereby limiting the extendability of plastic in this field.

The medical and pharmaceutical industries are continually searching for micro devices of reduced sizes, with multiple thousands of wells with diameters on the order of 100 microns and channels connecting selective wells at different levels within the array. Yet, once these micro devices are made available, there still remains a need in the art for implementing and integrating such micro devices to the rest of the macro instrumentation that is used for analyzing or testing the reagents.

SUMMARY OF INVENTION

Bearing in mind the problems and deficiencies of the prior art, it is therefore an object of the present invention to provide a method of integrating a micro device having micro wells and micro channels to a macro field of laboratory instrumentation.

It is another object of the invention to provide a method of making and the resultant ceramic micro device having at least micro wells with a optical micro plugs for integrating the ceramic micro device to macro instrumentation used for analyzing and testing various combinations of reagents provided within the micro wells.

Yet another object of the invention is to provide a method of making and the resultant ceramic micro device having micro wells and micro channels connecting selected micro wells whereby the ceramic micro device has optical micro plugs for integrating the ceramic micro device to macro instrumentation.

Another object of the invention is to provide a method of making and the resultant ceramic micro device having at least micro wells with optical micro plugs whereby the ceramic micro device is a laminated body.

Still another object of the invention is to provide a method of making and the resultant ceramic micro device having at least micro wells with optical micro plugs whereby the ceramic micro device is a sintered body.

Another object of the invention is to provide a method of making and the resultant ceramic micro device having at least micro wells with optical micro plugs whereby the optical micro plugs may be lenses, conductive micro plugs, non-conductive micro plugs, heaters, coolers, magnets, sensors, and combinations thereof.

Still other objects and advantages of the invention will in part be obvious and will in part be apparent from the specification.

The above and other objects, which will be apparent to those skilled in art, are achieved in the present invention, which is directed to a ceramic micro well plate that includes a first ceramic greensheet having at least one vertical opening therein. This vertical opening is a reaction chamber of the micro well plate. A second ceramic greensheet also has at least one vertical opening therein, which is aligned with the vertical opening in the first ceramic greensheet. The ceramic micro well plate further includes an optical micro plug in vertical opening in the second ceramic greensheet, whereby this optical micro plug allows viewing of the reaction chamber of the micro well plate.

In this aspect of the invention, the first and second ceramic greensheets may be either laminated or sintered. The optical micro plug is composed of an optically effective material including, for example, PDMS, PDMS plus a low concentration of capture molecules, glass, silica, ceramic, polymer and combinations thereof.

Depending upon the material selected to make the optical micro plug, such optical micro plug may be a lens, magnet (either permanent or non-permanent), sensor (e.g., temperature sensor, florescence sensor, etc.), heater, cooler, a conductive or non-conductive optical micro plug, or it may even include marker molecules residing therein.

In another aspect, the invention is directed to a ceramic micro well plate having a first ceramic greensheet with a first plurality of vertical openings therein. These plurality of vertical openings within the first greensheet are a plurality of reaction chambers of the ceramic micro well plate. The ceramic micro well plate also includes a second ceramic greensheet having a plurality of horizontal openings therein, whereby selected ones of the horizontal openings connect selected ones of the vertical openings in the first greensheet. The ceramic micro well plate also includes a third ceramic greensheet that also has a plurality of vertical openings therein that are aligned with the first plurality of vertical openings in the first ceramic greensheet. Within the vertical openings in the third greensheet are a plurality of optical micro plugs. These plurality of optical micro plugs are aligned with the first plurality of vertical openings in the first greensheet (i.e., the reaction chambers) to allow viewing of the reaction chambers of the micro well plate.

In yet another aspect, the invention is directed to a method of forming a ceramic micro well plate. The method includes providing a first ceramic greensheet and then forming a first plurality of vertical openings in the first ceramic greensheet. Each of these plurality of vertical openings in the first ceramic greensheet are reaction chambers of the micro well plate. A second ceramic greensheet is then provided, and a second plurality of vertical openings formed therein. The first plurality of vertical openings in the first ceramic greensheets are then aligned with the second plurality of vertical openings in the second ceramic greensheet. Once aligned, an optically effective material is deposited into the second plurality of vertical openings in the second ceramic greensheet to form a plurality of optical micro plugs, whereby the optical micro plugs allow viewing of the reaction chambers of the micro well plate. Optionally, a third ceramic greensheet may be provided, and a plurality of horizontal openings formed therein. This third ceramic greensheet is positioned between the first and second ceramic greensheets such that selected ones of the plurality of horizontal openings connect selected ones of the first plurality of vertical openings, while the optical micro plugs are aligned with the first plurality of vertical openings being the reaction chambers.

BRIEF DESCRIPTION OF DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION

In describing the preferred embodiment of the present invention, reference will be made herein to FIGS. 1A-3C of the drawings in which like numerals refer to like features of the invention.

The present invention is directed to integrating a miniaturized ceramic microfluidic device, having micro arrays with microscaled reaction chambers, i.e., microscale wells, to macroscaled analytical instrumentation used for analyzing and/or testing various reagents, as well as for diagnostic applications. This is accomplished by providing each of the micro reaction chambers with micro plugs, preferably optical micro plugs or windows, that allow for such integration. For example, the micro plugs of the invention may be provided within miniaturized ceramic microfluidic devices having multiple thousands of wells with diameters on the order of 100 microns and channels connecting selective wells at various levels within the array, such as those miniaturized ceramic microfluidic devices disclosed in related co-pending U.S. patent application Ser. No. 10/338,093 entitled "Multichannel and Multilayer Pharmaceutical Device," the subject matter of which is incorporated by reference.

Figure 1A:
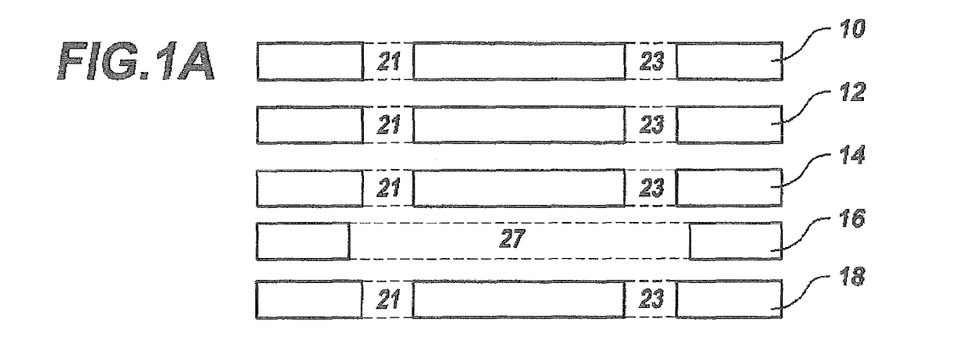
FIGS. 1A-1C are cross sectional views of alternate embodiments of the invention showing a plurality of greensheets having vertical and horizontal openings for forming a ceramic microfluidic well plate with a plurality of optical micro plugs that allow the ceramic well plate to be integrated with macro analytical instrumentation, whereby the optical micro plugs may be formed before or after lamination and sintering processes.
Figure 1B:
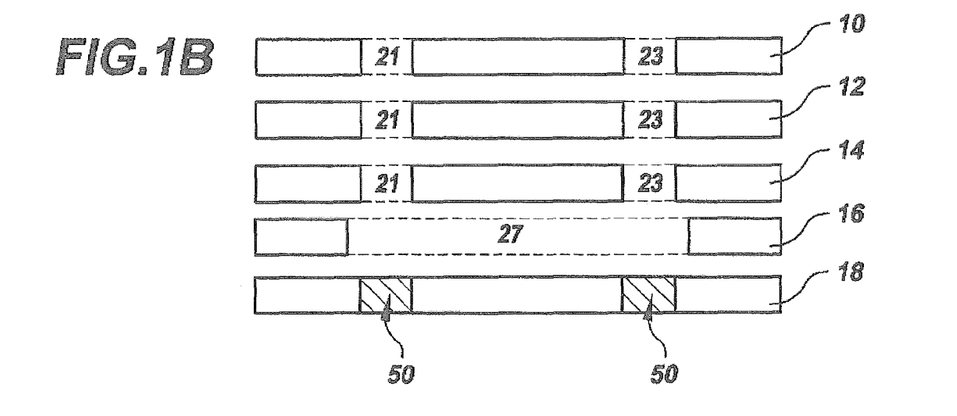
Figure 1C:
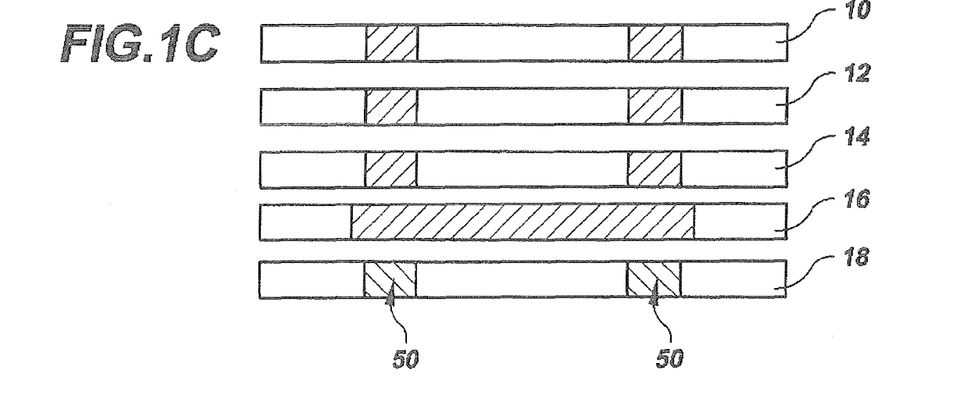

In forming the instant microfluidic device having micro reaction chambers with optical micro plugs, a plurality of greensheets are provided. For example, as shown in FIGS. 1A-1C, greensheets 10, 12, 14, 16 and 18 may be provided. These greensheets may be composed of a material including, but not limited to, alumina, glass, ceramic, aluminum nitride, borosilicate glass and mixtures thereof.

Selected greensheets are provided with a number of vertical openings, such as greensheets 10, 12, 14 and 18 having vertical openings 21 and 23, while other selected greensheets are provided with horizontal openings, such as greensheet 16 having horizontal opening 27. It should be appreciated that the plurality of greensheets may be provided with any number of vertical openings and horizontal openings, in any desired configuration, for allowing the horizontal openings to selectively connect and link selected vertical openings. That is, the greensheets may be provided with arrays of thousands of openings, whereby selected vertical openings are connected to each other or linked via thousands of horizontal openings.

In the preferred embodiment, the diameter of each of the vertical openings may be about 20 microns or more, while the horizontal openings may have widths of about 20 microns, or more, and lengths of a minimum of about 20 microns. For illustration purposes only, and not to limit the invention in any manner, opening 27 in greensheet 16 is shown having a length greater than twice the diameter of vertical openings 21 and 23 in greensheets 10, 12, 14 and 18. However, it should be appreciated that the diameters used in fabrication ultimately depend upon the particular application and technical variables, such as, viscosity of the chemicals/reagents that are to be provided within such microscaled wells, the surface tension/activity of the such chemicals/reagents, the desired quantity of chemicals/reagents, as well as the desired flow rates, capillary action and/or forced flow, and the like.

The vertical openings and horizontal openings may be provided within the plurality of greensheets using known techniques including, but not limited to, punching the greensheet material out by mechanical punching, laser drilling, e-beam drilling, sandblasting and high pressure liquid jets. However, micromolding by pressing the material to the side and distorting the greensheet is undesirable as the resultant desired well and channel position accuracy with respect to each other is very small, e.g. a few microns, and the distortions introduced by material displacement techniques are a significant obstacle to providing the desired accuracy. The horizontal openings are generally rectangular openings within the greensheets, while the vertical openings are generally circular openings within the greensheets.

As shown in FIG. 1A, the vertical openings 21 and 23 and horizontal openings 27 in all the greensheets may remain unfilled. The vertical openings and horizontal openings may remain unfilled if there is no concern that pressures during handling or other operations will distort them. Alternatively, as shown in FIG. 1B the vertical openings 21 and 23 and horizontal openings 27 in greensheets 10, 12, 14 and 16 may remain unfilled while the vertical openings 21 and 23 in greensheet 18 are provided with an optically effective material. Still further, as is shown in FIG. 1C, the vertical openings 21 and 23 and horizontal openings 27 in greensheets 10, 12, 14 and 16 may be filled with a fugitive material while the vertical openings 21 and 23 in greensheet 18 are provided with the optically effective material. This fugitive material may be a material that is burned-off or removed during or after lamination of the greensheets, such as, a paste deposited into the openings and openings within the greensheets. In filling the openings, the fugitive material will depend on the material of the greensheet.

For instance, the fugitive materials may be any compatible material that leaves no residue after it leaves, such as an organic material including, but not limited to, terepthalic acid, carbon, or other organic materials. The fugitive material is removed by heating it past its boiling or subliming temperature, so that the material evaporates into the ambient. Alternatively, the fugitive material may be removed by burning, that is, contacting the fugitive material with a reactant gas to from a gaseous substance that is dissipated into the ambient.

Alternatively, the fugitive materials may be combined with a matrix material for formation of a porous material upon sintering within either the vertical openings and/or the horizontal openings. This matrix material may include, but is not limited to, ceramics such as alumina, glass ceramic, aluminum nitride and borosilicate glass. Either the vertical openings, the horizontal openings or both, where the vertical well openings and horizontal channels are to be formed, are filled before sintering with a filler material that is a mixture of the fugitive material and the matrix material such that upon sintering, a porous matrix having open pores is formed whereby the porous matrix permits the passage of a fluid through it from vertical opening 21 to vertical opening 23. Thus, a continuous open structure remains in an open-pore matrix after sintering to permit the passage of a test material through the pores from one side of the present microfluidic well plate 50 to the other. It should also be appreciated that the unsintered porous body in the horizontal channel opening allows for the formation of controlled open volume and channel dimensions. Also, the unsintered porous body in the channel helps from channel collapse during sintering process. The fugitive material is preferably not formed in the vertical openings where the optical micro plugs are to be formed, e.g., vertical openings 21 and 23 in greensheet 18.

Figure 2A:
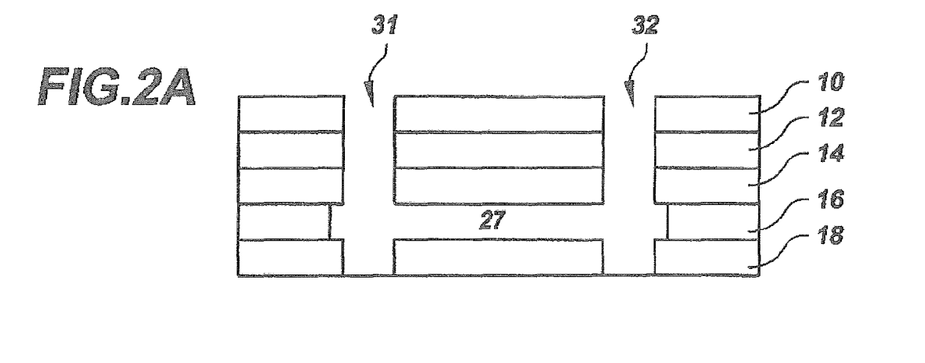
FIGS. 2A-2C are cross sectional views of the alternate embodiments of FIGS. 1A-1C, respectively, showing the plurality of greensheets of such alternate embodiments laminated to one another.
Figure 2B:
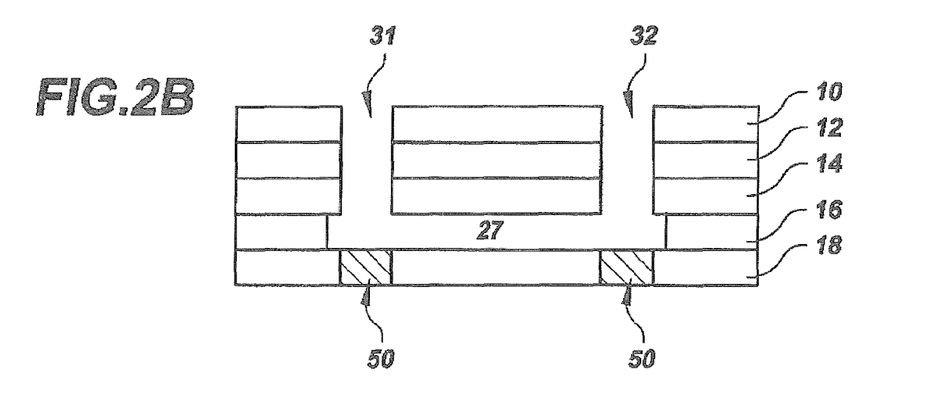
Figure 2C:
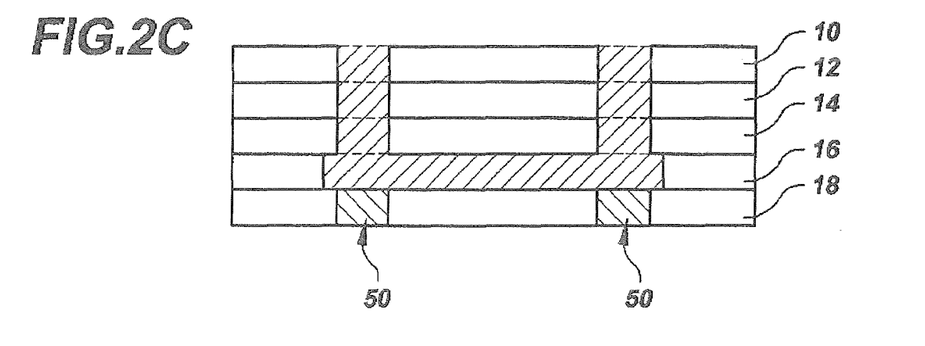
Figure 3A:
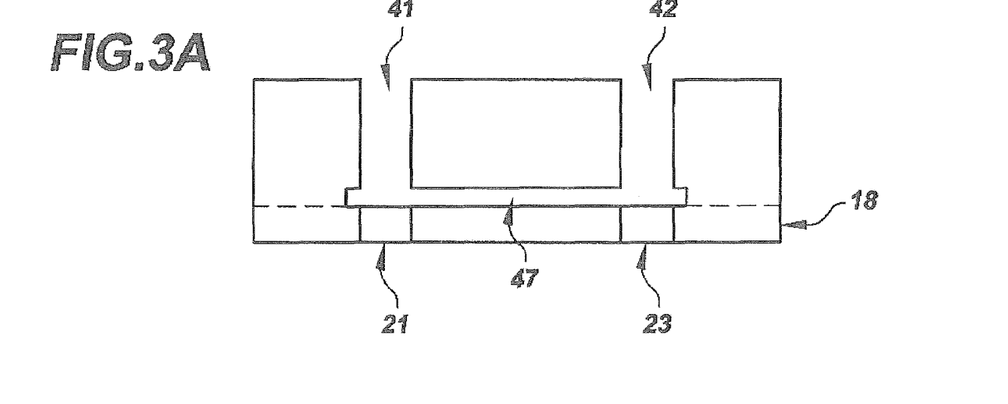
FIGS. 3A-3C are cross sectional views of the alternate embodiments of FIGS. 2A-2C, respectively, showing the plurality of laminated greensheets after sintering.
Figure 3B:
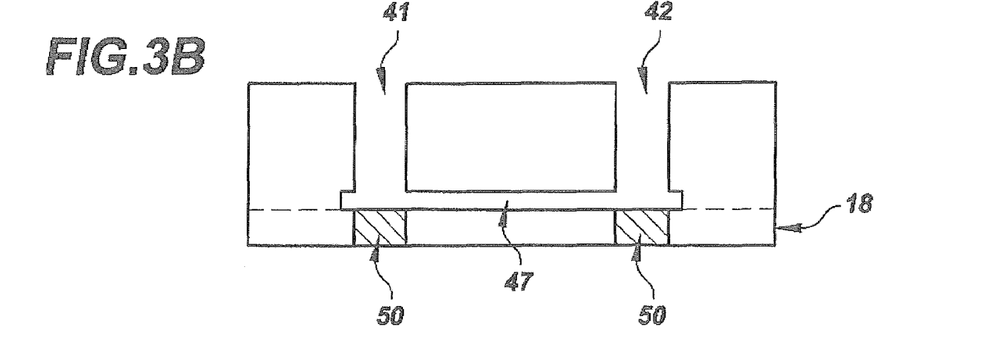
Figure 3C:
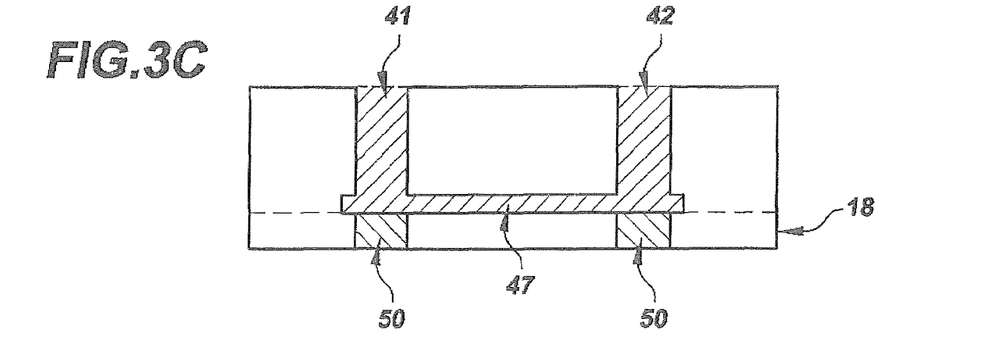

In the process of forming the resultant microfluidic well plates shown in FIGS. 3A-3C, the greensheets are first stacked and laminated. Referring to FIGS. 2A-2C, the greensheets 10, 12, 14 and 16 are stacked such that the vertical openings 21 and 23 residing within corresponding greensheets 10, 12 and 14 are first aligned to one another. These aligned vertical openings 21 and 23 form vertical openings 31 and 32 through the stack of aligned greensheets 10, 12 and 14. The horizontal opening 27 in greensheet 16 is provided in contact with both aligned vertical openings 31 and 32, such that, the horizontal opening 27 both links vertical opening 31 to vertical opening 32, as well as extend the length of each vertical openings 31 and 32. Greensheet 18 is then positioned under greensheet 16 such that vertical openings 21 and 23 within greensheet 18 reside at a backside of the horizontal opening 27. These vertical openings 21 and 23 within greensheet 18 are also in alignment with vertical openings 31 and 32, as is shown in FIGS. 2A and 2B.

Optionally, the ceramic microfluidic well plate may not be provided with horizontal openings 27. In this aspect, greensheet 18 is positioned under greensheet 14 such that vertical openings 21 and 23 within greensheet 18 are in alignment with and contact vertical openings 31 and 32, respectively.

The aligned greensheets 10, 12, 14, 16 and 18 are then laminated to one another. The lamination process of the invention involves heat, pressure and time. The preferred lamination pressure is under 800 psi, the temperature is under 90° C., and the lamination time is less than about 5 minutes. More preferably, the lamination pressure ranges from about 300 psi to about 2,000 psi, the temperature ranges from about 60° C. to about 90° C., and the lamination time ranges from about 1 minute to about 5 minutes.

Upon completion of laminating the stack of greensheets, the laminated greensheets are then sintered in a conventional process to form the ceramic microfluidic well plates shown in FIGS. 3A-3C. It should be appreciated and understood that the sintering process and conditions are dependent upon the material of choice as well as the binder system used to form the greensheets. Referring to FIGS. 3A-3C, the sintered ceramic microfluidic well plates may include vertical micro well openings 41 and 42 (formed from the vertical openings 31 and 32) and optional horizontal channel(s) 47 (formed from the horizontal opening 27). The horizontal channel 47 connects and links the vertical micro well openings 41 and 42 to one another. However, wherein the laminated greensheet stack does not include a greensheet having a channel opening 27 (not shown), the ceramic microfluidic well plate will not be provided with horizontal channel(s) 47. As discussed in detail above, the vertical micro well openings 41 and 42 and/or horizontal channel(s) 47 may be filled with a material, such as fugitive material shown in FIG. 3C, or they may be remain empty (unfilled) as shown in FIGS. 3A-3B.

A critical feature of the invention is that in the resultant ceramic microfluidic well plates, whether the well openings and/or channels are filled or unfilled, the remaining vertical openings 21 and 23 (residing within former greensheet 18) located at a backside of the horizontal channel 47, or at a backside of the vertical micro well openings 41 and 42, are completely filled with an optically effective material for formation of the plurality of optical micro plugs or windows 50. This material is preferably a transparent material for formation of transparent optical micro plugs. The preferred material may include, but is not limited to, Poly Dimethyl Siloxane (PDMS), PDMS plus a low concentration of capture molecules, glass, silica, polymer and the like. Capture molecules are defined herein as a large number of highly specific molecules showing high affinity to their target for identification and quantification. These capture molecules may include, for example, markers including, but not limited to, biomarkers and markers for the identification of proteins, as well as capture molecules of highly specific molecules for the mixing of complex chemical molecules, and the like. PDMS is preferable as it is substantially transparent, has excellent molding characteristics and shrinkage characteristics (usually less than 0.5%), it has sufficient sticking characteristics such that once within the openings 21 and 23 it adheres sufficiently strongly therein and to the greensheet material. PDMS is also helpful during incubation cycles, and its background fluorescence characteristics are desirable in pharmaceutical applications as it emits minimal background noise (e.g., substantially near zero). An essential feature of the invention is that the plurality of optical micro plugs or windows allow for the resultant ceramic microfluidic well plate to be integrated or implemented with macro analytical instrumentation for analyzing samples within the micro well openings.

Wherein the sintered ceramic plate includes horizontal channel(s) 47, the plurality of micro plugs are formed at a backside of the horizontal channel(s) 47 in locations that are in alignment with the vertical micro well openings 41 and 42. Alternatively, wherein the sintered ceramic plate does not include horizontal channel(s) 47, the plurality of micro plugs are formed at a backside of, and in direct contact with and aligned to the vertical micro well openings 41 and 42. In both aspects, it is critical that the plurality of micro plugs are formed in alignment with each of the plurality of vertical micro well openings 41 and 42 for allowing macro analytical instrumentation to process, test and/or analyze samples introduced within the vertical micro well openings 41 and 42.

The micro well openings, such as micro well openings 41 and 42, are micro reaction chambers of the micro well plate, where an array of substances $A_1$-$A_n$, $B_1$-$B_n$, etc. are introduced therein, such that these substances mix and interact with one another in the micro reaction chambers. Each of these micro reaction chambers has located at, at least one end thereof the instant optical micro plugs for allowing the macro analytical instrumentation to analyze, test or view the reaction occurring within each of such micro reaction chambers.

In accordance with the invention, depending on the material selected to form the optical micro plugs 50, the optical micro plugs may be glass micro plugs, polymer micro plugs, such as plastic micro plugs, ceramic, and the like. Further, depending on the material selected in combination with the ultimate end use of the optical micro plugs 50, the optical micro plugs may include lenses, conductive micro plugs, non-conductive micro plugs, heaters, coolers, permanent magnets, non-permanent magnets, sensors (which may include plugs with biomarkers or capture molecules), or combinations thereof.

For example, the optical micro plugs 50 may be lenses for integrating the individual micro well reaction chamber openings to macro instrumentation for magnification purposes, or supplying a light or thermal energy to such reaction chambers. Optical micro plug lenses may be formed by providing a desired material capable of forming a lens, such as, but not limited to, glass powder, glass frit, organics that can form lens material (such as, polycarbonate resin) or combinations thereof, and optionally mixing such materials with removable binders, if necessary. These materials may be provided as pastes which can be screened into the micro openings. Once screened therein, surfaces of the paste are shaped into desired lens pattern (s) by known molding techniques, and then a solid lens is formed by curing or densifying to desired characteristics respectively by known arts such as thermal or UV treatment, or sintering. The optical micro plug lenses may be formed after the formation of glass plugs, such as by depositing a plastic or low melting glass on top of the individual plugs 50, or alternatively, by coating the entire exposed surface of greensheet layer 18 with a plastic or low melting glass such that the plugs 50 are at least provided with such materials for formation of the lenses.

Wherein it is desired that the optical micro plugs 50 be optical micro plug magnets (either permanent or nonpermanent), the materials used to form such optical micro plug magnets may include, but are not limited to, barium, strontium ferrites, and other such ceramic magnetic materials. It is preferred that the chosen ceramic magnetic materials be capable of being cosintering with ceramic materials like glass ceramic with proper additives. The magnetic materials may be in the form of a paste, which is deposited into vertical and/or horizontal openings (respectively, via and/or channel openings) to form the optical micro magnetic plugs. For example, the optical micro plugs 50 may be composed of ceramic magnet materials that are screened into the greensheet 18 and then sintered to form a dense magnet. However, it should be appreciated that the foregoing example is only one of a number of approaches for forming the optical micro magnetic plugs of the invention, which will be apparent to those skilled in the art in light of the foregoing description.

The optical micro plugs 50 may also be formed as heaters or coolers depending on the thermal conductivity of the plug material. These optical heater/cooler micro plugs may be either cosintered or formed after lamination. In so doing, external heating and/or cooling may be integrated with the high thermal conductivity micro plugs to achieve the desired heating or cooling effects. The materials used to form the optical heating/cooling micro plugs may include a metal, which are known for their high thermal conductivity and can be cosintered with ceramic plates, as well as high thermal conductivity organics, high thermal conductivity composites with metal particles, and the like. Further, these heater/cooler micro plugs may protrude from the surface of the ceramic plate (not shown) for providing additional control to such heater/cooler micro plugs.

Alternatively, or in addition to any of the above, the optical micro plugs 50 may be formed as sensors. These optical micro sensor plugs may be for temperature control, chemical identification, protein identification, biomarker identification, electrical responses, magnetic responses, and the like. The material choice of the micro plug is dependent upon the particular sensor application. For example, in the case of chemical identification, the plugs may be predoped to sense certain chemical(s) or chemical reaction(s), such as, certain capture molecules being mixed with poly dimethyl siloxane to form the optical sensor micro plugs for sensing bound biomolecules by fluorescence.

The optical micro plugs 50 may be solid bodies that completely fill the vertical openings 21 and 23, whereby each plug is directly integrated to the macro instrumentation. Alternatively, the optical micro plugs 50 may be a fine porous medium within vertical openings 21 and 23. Wherein each optical micro plug is a fine porous medium, prior to integrating the optical micro plugs 50 to macro instrumentation, a chemical component is deposited within each optical micro plug, at an exposed side thereof. In so doing, this chemical component reacts with the material of the fine porous medium of the micro plug for allowing the subsequently integrated macro instrumentation to examine the reaction or chemicals within the micro reaction chamber openings. For example, wherein the optical micro plugs 50 are optical sensor micro plugs having porous bodies, doped capture molecules for sensing bound biomolecules are distributed uniformly within the micro plug and exposed. This enables analytical macro instrumentation (e.g., mass spectrometry) integrated with the optical sensor micro plugs to sense (or assess), in real time, both quantitatively and qualitatively measures of bioassay reactions. Alternatively, the porous micro plugs may deposit resultant assays onto a substrate (which is in direct contact with all micro plugs with no cross-contamination) as an array of samples to be subsequently analyzed by macro instrumentation.

Referring again to the drawings, the plurality of optical micro plugs 50 may be formed before lamination, as is shown in FIGS. 1B and 1C, after lamination but before sintering, as is shown in FIGS. 2B and 2C, or even after sintering, as shown by the illustrations of FIGS. 3A and 3B. That is, FIG. 3A is an unfilled sintered ceramic plate which is filled with optically effective material in the remaining vertical openings 21 and 23 to form the optical micro plugs 50 shown in FIG. 3B. These optical micro plugs may be formed by screening, extrusion and the like. In all of the above approaches, the plurality of optical micro plugs may be formed by screening (chemically bonding), extrusion (mechanically bonding), and the like. For instance, the greensheets may be composed of material A, while the optically effective material of the micro plugs is material B. Upon screening the material B into the openings within the greensheet, these materials A and B react with one another such that they chemically bond to one another, thereby chemically bonding the optical micro plugs to the greensheet.

In forming the optical micro plugs 50 before sintering, vertical openings 21 and 23, within greensheet 18, may be completely filled with optically effective material either before or after lamination. The optically effective material may be screened or extruded into the vertical openings 21 and 23. Optically effective materials that are capable of withstanding the sintering process to form micro plugs 50 include, but are not limited to, glass, ceramic and the like. Upon completion of sintering, the optically effective material in vertical openings 21 and 23 in greensheet 18 becomes a dense material that completely fills such vertical openings to form the optical micro plugs 50.

Alternatively, in forming the optical micro plugs 50 after sintering, the laminated greensheets, having unfilled vertical openings 21 and 23 within greensheet 18, are sintered to form the sintered ceramic well plate of FIG. 3A having empty vertical openings 21 and 23 (of greensheet 18). These remaining vertical openings 21 and 23 within greensheet 18 are then completely filled with an optically effective material to form the plurality of optical micro plugs 50, as shown in FIG. 3B.

The optically effective material may include, but is not limited to, low melting glass, polymer (e.g., PDMS) and the like. This optically effective material may be provided within the vertical openings 21 and 23 of the sintered ceramic well plate by screening, extrusion, and the like. The optically effective material may be either chemically bonded to the ceramic well plate or mechanically bonded to the ceramic well plate.

Further, without departing from the novel concept of the invention, wherein laminated non-porous sheets shown in FIGS. 2B and 2C, have optical micro plugs 50 already formed therein, adhere sufficiently tightly to one another so that leakage of samples introduced into vertical openings 31 and 32 does not occur, thereby not requiring sintering of the laminated stack, this laminate ceramic plate may be used as the resultant ceramic micro well plate. That is, the vertical openings 31 and 32 are used as the micro well opening reaction chambers of the ceramic plate in which substances $A_1$-$A_n$, $B_1$-$B_n$, etc. are introduced therein for the mixing and interacting thereof. Each vertical micro well opening 31 and 32 (micro reaction chambers) has located at, at least one end thereof the instant optical micro plugs for allowing macro analytical instrumentation to analyze, test or view the reaction occurring within each of such micro reaction chambers.

Whether the micro well opening reaction chambers are provided either before (FIGS. 2B-2C) or after (FIGS. 3B-3C) sintering, each micro well opening may be about 20 microns or more, preferably about 50-250 microns, while the horizontal channels may have widths of about 20 microns, or more, and lengths of a minimum of about 20 microns. The shapes of the micro well openings exposing a substance may be circular, rectangular, smooth, rough, or combinations thereof. The total thickness of the resultant ceramic micro well plate with the optical micro plugs 50 be any desired amount, but preferably is under 1 mm. The thickness of each greensheet depends on the application, but preferably ranges from about 50 microns-500 microns.

Thus, in accordance with the invention, a window or optical micro plug is integrated with the micro reaction chamber openings of the ceramic well plate for allowing a macro field of laboratory instrumentation to examine the reaction or chemicals within the micro reaction chamber openings. For instance, wherein target specific molecules, such as molecules A, are entirely embedded within the optical micro plug having an affinity to target molecules B, C or the like within a mix reaction solution in the reaction chamber, then the optical micro plugs of the invention may be used as a sensor, or a means to communicate that to the macro instrumentation (e.g., fluorescence), etc. In this example, the macro instrumentation that the well plates may be integrated with, via the optical micro plugs, may be an inverted optical microscope for viewing and detecting fluorescence, i.e., fluorescent markers, within the solution in the reaction chamber through the transparent optical micro plugs. Further, a low fluorescent background glass plug may be suitable for confocal image analysis, fluorescent polarization, fluorescence correlation spectroscopy, and the like.

Optionally, the optical micro plugs 50 of the invention may be formed at top surfaces and bottom surfaces of selected micro well reaction chamber openings within the resultant micro well plate. That is, in addition to green sheet 18 having the optical micro plugs 50, another greensheet is provided on the opposite side of the laminated or sintered greensheets, e.g., over the exposed surface of greensheet 10 (on the side opposing greensheet 12), such that vertical openings may be provided within this additional greensheet, and then optical micro plugs 50 of the invention formed in selected ones of these vertical openings. In so doing, selected ones of the vertical well openings (reaction chambers) will have optical micro plugs at top and bottoms surface thereof, while others of the vertical well openings (reaction chambers) will have optical micro plugs only at bottom surfaces thereof. It is important to leave at least one of the vertical well openings open at, at least one surface thereof for introducing the various samples, chemicals, reagents, etc. therein for reacting within the vertical well opening.

Alternative ways of forming the ceramic well plate having optical micro plugs include using a densifiable material for the greensheets and filling the openings with a non-densifiable material in order to preserve the dimensions of such openings. For example, the matrix material (greensheets) may be an inorganic phase like alumina mixed with glass frit for densification, whereas the non-densifiable phase in the openings (including vertical and horizontal openings) could be just larger ceramic particles like alumina.

Additionally, the material in the openings may be one that forms a non-porous sheath upon being sintered, so that the openings receive a liner. In this aspect, the sheath has alternate surface energy/activity than the body of the ceramic well plate. The material for the sheath can be organic, inorganic, metal or composite. The sheath formation may be due to chemical decomposition between a first material in the laminate and a second material in the filler or in the ambient gas and/or the sheath formation may be due to vapor phase deposition. As another option, the liner could be produced by a vapor emitted by the filler material that deposits on the walls or reacts with a material contained in the laminate.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A ceramic micro well plate comprising:
   a first ceramic greensheet;
   at least one vertical opening in said first ceramic greensheet, said vertical opening in said first ceramic greensheet being a reaction chamber of said micro well plate;
   a second ceramic greensheet under said first ceramic greensheet;
   at least one vertical opening in said second ceramic greensheet that is aligned with said at least one vertical opening in said first ceramic greensheet; and
   an optical micro plug residing within and entirely filling said at least one vertical opening in said second ceramic greensheet, whereby said optical micro plug allows viewing of said reaction chamber of said micro well plate by residing at a bottom thereof.

2. The ceramic micro well plate of claim 1 wherein said first and second ceramic greensheets are laminated to one another.

3. The ceramic micro well plate of claim 1 wherein said first and second ceramic greensheets are sintered greensheets.

4. The ceramic micro well plate of claim 1 wherein said optical micro plug comprises an optically effective material selected from the group consisting of PDMS, PDMS plus a low concentration of capture molecules, glass, silica, ceramic, polymer and combinations thereof.

5. The ceramic micro well plate of claim 1 wherein said optical micro plug comprises a lens.

6. The ceramic micro well plate of claim 1 wherein said optical micro plug comprises a magnet.

7. The ceramic micro well plate of claim 1 wherein said optical micro plug comprises a sensor.

8. The ceramic micro well plate of claim 1 wherein said optical micro plug includes marker molecules residing therein having high affinity to their target for identification and quantification of said target.

9. The ceramic micro well plate of claim 1 wherein said optical micro plug comprises a conductive optical micro plug.

10. The ceramic micro well plate of claim 1 wherein said optical micro plug comprises a non-conductive optical micro plug.

11. The ceramic micro well plate of claim 1 wherein said optical micro plug comprises a heater.

12. The ceramic micro well plate of claim 1 wherein said optical micro plug comprises a cooler.

13. A ceramic micro well plate comprising:
   a first ceramic greensheet;
   a first plurality of vertical openings in said first ceramic greensheet, said first plurality of vertical openings in said first ceramic greensheet being a plurality of reaction chambers;
   a second ceramic greensheet under said first ceramic greensheet;
   a plurality of horizontal openings in said second ceramic greensheet, whereby each of said plurality of horizontal openings connect two or more of said first plurality of vertical openings in said first ceramic greensheet to one another;
   a third ceramic greensheet under said second ceramic greensheet;
   a second plurality of vertical openings in said third ceramic greensheet aligned with said first plurality of vertical openings in said first ceramic greensheet; and
   a plurality of optical micro plugs residing within and entirely filling said second plurality of vertical openings, said plurality of optical micro plugs aligned with said first plurality of vertical openings to allow viewing of said reaction chamber of said micro well plate by residing at a bottom thereof.

14. The ceramic micro well plate of claim 13 wherein said plurality of optical micro plugs comprise a transparent material selected from the group consisting of PDMS, PDMS in combination with capture molecules, glass, silica, ceramic, polymer and combinations thereof.

15. The ceramic micro well plate of claim 13 wherein said plurality of optical micro plugs are selected from the group consisting of optical micro plug lenses, optical conductive micro plugs, optical non-conductive micro plugs, optical micro plug heaters, optical micro plug coolers, optical micro plug magnets, optical micro plug sensors and combinations thereof.

16. A method of forming a ceramic micro well plate comprising:
   providing a first ceramic greensheet;
   forming a first plurality of vertical openings in said first ceramic greensheet, each of said first plurality of vertical openings in said first ceramic greensheet being reaction chambers of said micro well plate;
   providing a second ceramic greensheet;
   forming a second plurality of vertical openings in said second ceramic greensheet;
   providing said second ceramic greensheet under said first ceramic greensheet;
   aligning said first plurality of vertical openings in said first ceramic greensheets with said second plurality of vertical openings in said second ceramic greensheet; and depositing an optically effective material to fill said second plurality of vertical openings in said second ceramic greensheet to form a plurality of optical micro plugs within said second plurality of vertical openings, whereby said optical micro plugs reside at bottoms of said reaction chambers of said micro well plate to allow viewing of said reaction chambers of said micro well plate.

17. The method of claim 16 further including the steps of:

providing a third ceramic greensheet;

forming a plurality of horizontal openings in said third ceramic greensheet; and positioning said third ceramic greensheet between said first and second ceramic greensheets such that each of said plurality of horizontal openings connect two or more of said first plurality of vertical openings in said first ceramic greensheet to one another while said plurality of optical micro plugs are aligned with said first plurality of vertical openings being said reaction chambers.

18. The method of claim 16 further including laminating said first and second greensheets to form said micro well plate having said plurality of optical micro plugs.

19. The method of claim 18 further including sintering said laminated first and second greensheets to form said micro well plate having said plurality of optical micro plugs.

20. The method of claim 16 wherein said formed plurality of optical micro plugs are selected from the group consisting of optical micro plug lenses, optical conductive micro plugs, optical non-conductive micro plugs, optical micro plug heaters, optical micro plug coolers, optical micro plug magnets, optical micro plug sensors and combinations thereof.

* * * * *

UNITED STATES PATENT AND TRADEMARK OFFICE
CERTIFICATE OF CORRECTION

PATENT NO.        : 7,645,423 B2                                                    Page 1 of 1
APPLICATION NO.   : 10/711071
DATED             : January 12, 2010
INVENTOR(S)       : Natarajan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1260 days.

Signed and Sealed this

Sixteenth Day of November, 2010

David J. Kappos
*Director of the United States Patent and Trademark Office*